United States Patent [19]

Ginsburg et al.

[11] Patent Number: 4,800,404
[45] Date of Patent: Jan. 24, 1989

[54] APPARATUS AND METHOD FOR TESTING VISUAL SENSITIVITY TO GLARE

[75] Inventors: Arthur P. Ginsburg; David W. Evans, both of Dayton; Kenneth Blauvelt, Centerville, all of Ohio

[73] Assignee: Vistech Consultants, Inc., Beavercreek, Ohio

[21] Appl. No.: 910,000

[22] Filed: Sep. 22, 1986

[51] Int. Cl.⁴ ............................ A61B 3/02; A61B 3/00
[52] U.S. Cl. ..................................... 351/243; 351/246
[58] Field of Search ................ 351/243, 237, 246, 232

[56] References Cited

U.S. PATENT DOCUMENTS 2,209,728  7/1940  Higley ................................. 351/243
2,795,993  6/1957  Leverett et al. .................... 351/243
3,684,355  8/1972  Molner ................................ 351/243
3,936,162  2/1976  Krakau et al. ..................... 351/246

Primary Examiner—Rodney B. Bovernick
Assistant Examiner—Jay P. Ryan
Attorney, Agent, or Firm—Biebel, French & Nauman

[57] ABSTRACT

Glare testing apparatus enclosed in a housing includes multiple discrete light sources for creating a glare condition in the field of view from an individual being tested to a target, and provision is made for selecting the location or locations of active glare sources, which includes a centrally located source of headlight glare, and a plurality of peripheral sources which can be energized selectively or collectively. Provision is also made for adjusting target luminance, glare intensity and the apparent distance between the target and the eye position in order to test near and far visual acuity under varied conditions of luminance and glare.

18 Claims, 3 Drawing Sheets

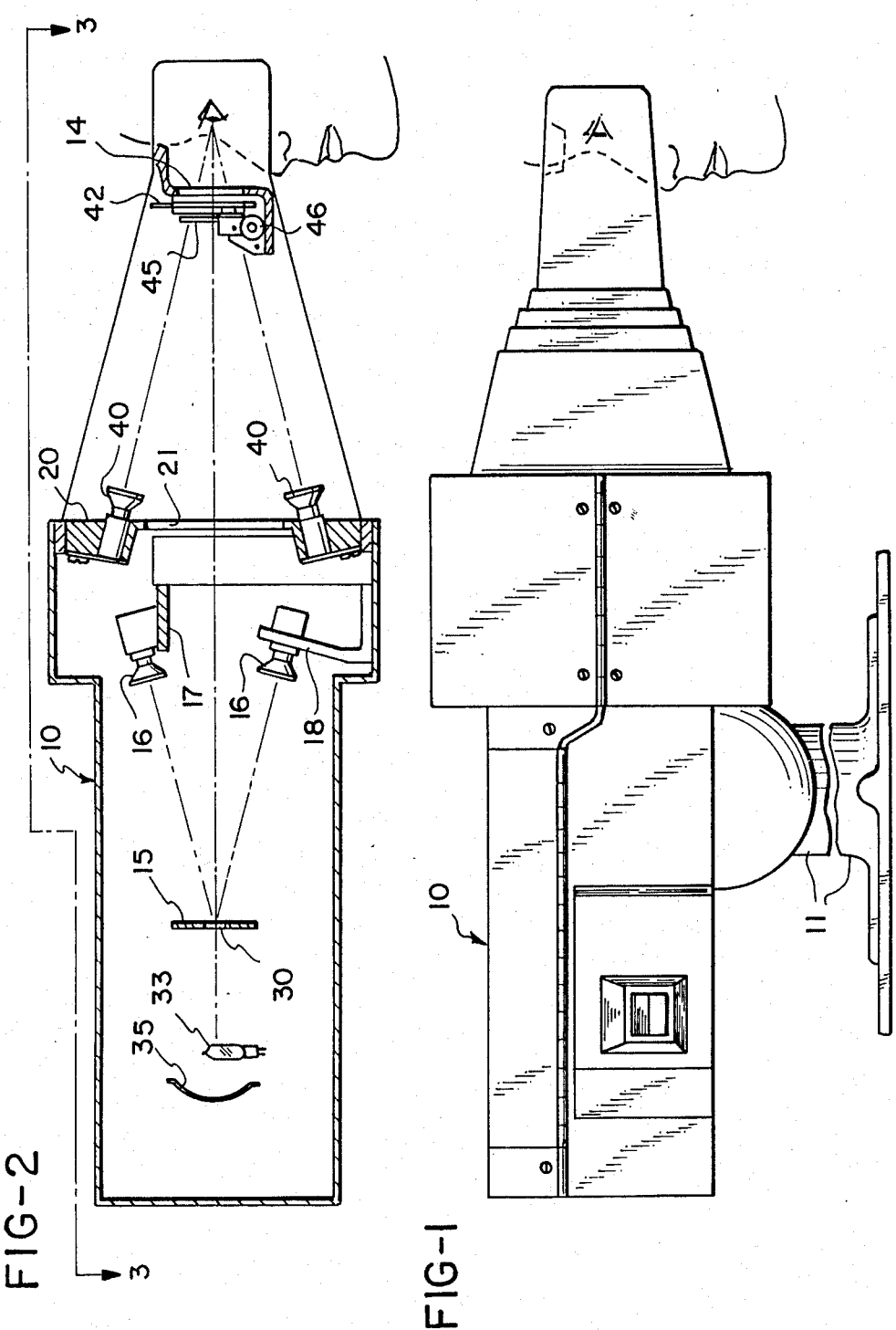

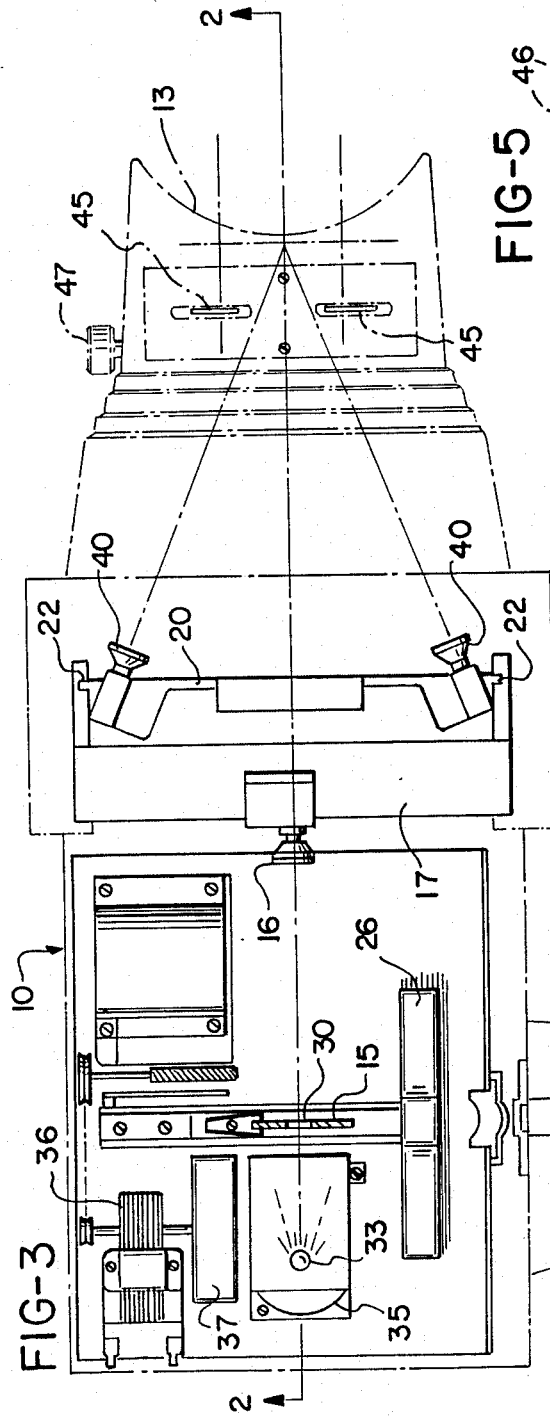
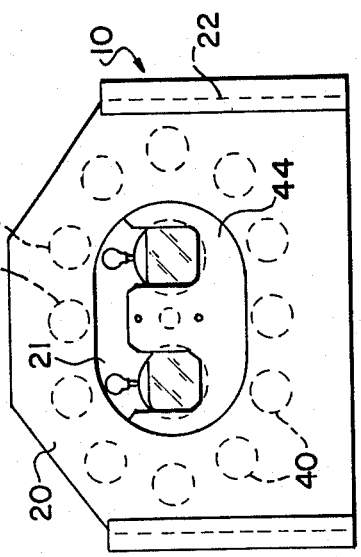
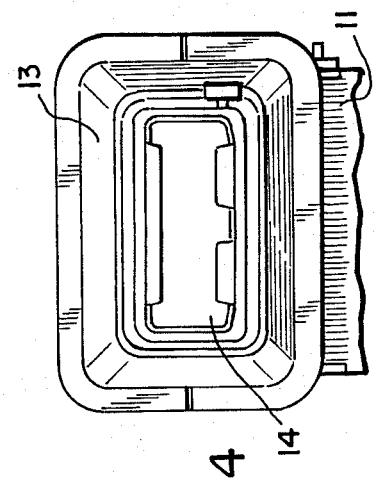

U.S. Patent   Jan. 24, 1989   Sheet 3 of 3   4,800,404
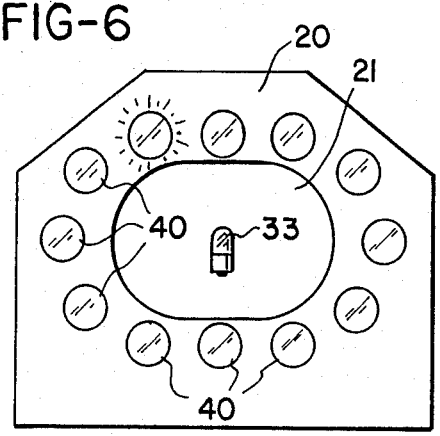
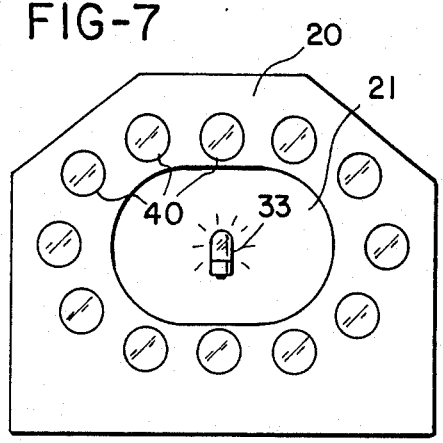
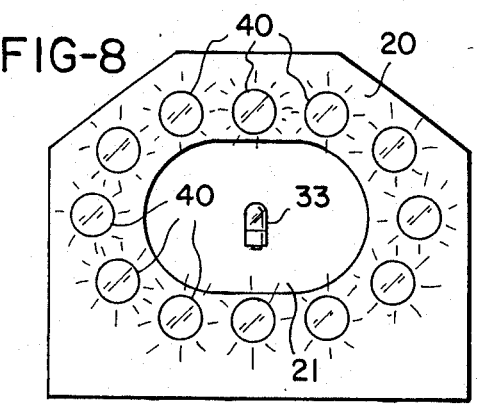
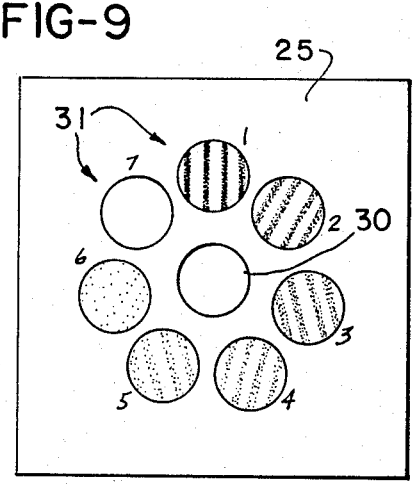
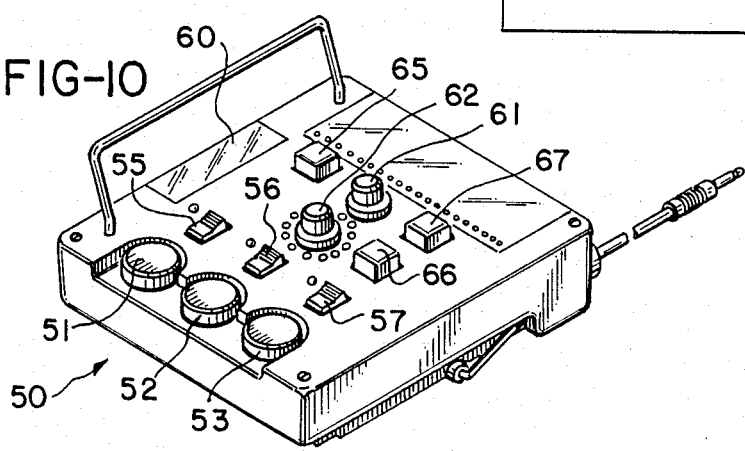

APPARATUS AND METHOD FOR TESTING VISUAL SENSITIVITY TO GLARE

BACKGROUND OF THE INVENTION

Ginsburg U.S. Pat. No. 4,365,873 discloses a technique for testing the visual sensitivity of an individual in terms of contrast sensitivity and spatial frequency response in conjunction with a chart having thereon a multiplicity of grating patches which vary in contrast, spatial frequency and angular orientation. In use, the chart is scanned beginning with the patches of maximum contrast and minimum frequency until the low contrast level or the high spatial frequency prevents the observer from detecting the gratings or their orientation. The threshold levels of the individual under test are quantified and compared to a norm.

SUMMARY OF THE INVENTION

A primary objective of the present invention is to provide methods and apparatus for testing the visual acuity of an observer with respect to and/or in the presence of glare which are simpler, more accurate and more versatile than any presently available.

A more specific object of the invention is to provide a glare testing apparatus wherein the testing is carried in conjunction with a target having thereon areas which differ in contrast, in spatial frequency and/or orientation, wherein there are selectively energizable glare sources located centrally of the target and also in peripheral and radial relation therewith, and wherein other options include adjustable target luminance, adjustable glare intensity, and provision for varying the apparent distance between the target and the eye position of the individual under test.

In a preferred embodiment of the invention, as described in detail below, all operating parts are enclosed within a single housing which includes means defining a fixed position for the head of the individual under test at a predetermined distance from the target to establish a field of view within the housing between the target and the eye position.

Provision is made within the housing for producing a glare condition within the observer field of view from selectively operable light beam sources located in peripheral relation with the target, at a radially spaced position from the center of the target, and at the center of the target. Further controls are provided for regulating the intensity of the glare sources and also for regulating the luminance of the target, together with provision for inserting optical lenses between the target and the observer so that with a single apparatus, tests can be made for near and far contrast sensitivity, visual acuity, three types of glare sensitivity, photo-stress, night vision and glare recovery.

Specific means and method steps by which the objectives of the invention are accomplished are described hereinafter in connection with the drawings.

BRIEF DESCRIPTION OF THE DRAWINGS

FIG. 1 is a side elevation illustrating testing apparatus in accordance with the invention;

FIG. 2 is a somewhat diagrammatic view taken generally on the line 2—2 of FIG. 3;

FIG. 3 is a somewhat diagrammatic plan view taken generally as indicated by the line 3—3 of FIG. 2;

FIG. 4 is an end elevation of the apparatus looking from right to left in FIG. 3;

FIG. 5 is a somewhat diagrammatic view taken as indicated by the line 5—5 of FIG. 3;

FIGS. 6, 7 and 8 are views similar to FIG. 5 and illustrating different glare conditions;

FIG. 9 is an illustration of one of the target charts, on an enlarged scale, utilized with the apparatus of FIGS. 1-8; and FIG. 10 is a perspective view of the control panel for the apparatus of FIGS. 1-7.

DESCRIPTION OF THE PREFERRED EMBODIMENT

Referring initially to FIGS. 1-3, the testing apparatus of the invention is enclosed in a housing indicated generally at 10 and mounted on a stand 11. The individual to be tested is positioned at the right-hand end of the apparatus as viewed in FIGS. 1-3, and that end of the housing includes a concave portion 13 which frames a generally rectangular viewing opening 14 for the observer and is proportioned to accommodate the observer's face and thus to locate the observer's eyes in proper position with the viewing opening 14 and the optical system within the housing.

The target 15, which includes test chart patterns as described below, is located inside the housing at a fixed distance from the eye position established by the curved housing face 13, satisfactory results having been obtained with this distance as 18 inches. The face of the target 15 is illuminated by a pair of light beam projectors 16 mounted on portions 17 and 18 of the glare ring assembly, the major part of which is a plate 20 having an open center 21 and having its side edges removably fitted in slots 22 in the wall of housing 10.

To provide increased versatility for the apparatus of the invention, the target 15 is one of a series of opaque charts 25, one of which is shown in FIG. 9, of the same size as a conventional 35-mm slide, and the apparatus is provided within the housing 10 with a conventional 35-mm slide changing mechanism including a magazine mounted to move lengthwise of housing 10 on a rack 26. A conventional arm 27 for actuating the slide changer projects from one side of the housing 10.

The typical chart 25 shown in FIG. 9 is a square card having a centrally located hole 30 therethrough surrounded by a series of areas or patches 31 which vary in contrast over a substantial range as described in the above Ginsburg patent. Preferably, each patch comprises parallel gray bars on a white background, with each patch having the bars therein at a different orientation with respect to the vertical from the bars in the adjacent patches on each side thereof, and preferably also, the patches of minimum and maximum contrast will be adjacent each other with the contrast in each of the other patches varying progressively around the series of patches.

In the Ginsburg patent, the chart has multiple rows of patches, the patches in each row differ in density but have the same spatial frequency, and the spatial frequency of the patches in each row differs from that of the patches in the other rows. Space limitations in the apparatus of the present invention make it impractical to provide more than one series of similar patches on a single chart, and the patches 31 in FIG. 9 correspond in spatial frequency and varied contrast to those in the top row in FIG. 1 of the Ginsburg patent, with the patch of maximum contrast eliminated because it calls for the least visual sensitivity.

The same principle of patches which differ from each other in spatial frequency is readily practiced with the apparatus of the invention by the use of multiple charts which are separately positionable in the viewing position by means of the slide changing mechanism as already described, so that, for example, a set of five charts will provide all of the variations in spatial frequency shown in the Ginsburg patent. Additional variation can be obtained using the same series of patches on several cards but changing the orientations of the patches from card to card. In addition, the patch positions are preferably numbered, as shown in FIG. 9, so that the individual under test can identify by number the location of each patch which he or she can detect.

When a chart 20 is located in the target position 15 shown in FIGS. 2 and 3, the hole 30 therein will be in direct alignment with a lamp bulb 33 which cooperates with a suitable reflector 35 to project a light beam directly through the hole 30 to the viewing position defined by the housing surface 13, thereby providing a source of central or headlight glare in the center of the field of view in which the individual under test observes the target. FIG. 3 also shows a motor 36 driving a fan 37 for dissipating the heat from the bulb 33, as in conventional slide projectors In addition to the central glare, provision is made for creating peripheral glare from an array of discrete light sources in the field of view in which the individual under test observes the target 15. The plate 20 having an open center 21 is mounted in the housing approximately midway between the viewing position 13 and the target 15, and multiple small light beam projectors 40, a total of twelve being shown, are mounted in this plate in surrounding relation with its center opening 21 to project a corresponding series of peripheral light beams toward the viewing opening 14. Provision is made, as described hereinafter, for actuating all of these beam projectors 40 simultaneously or any selected one thereof, and also for varying the intensity of the beams produced thereby.

Referring now to FIGS. 2, 3 and 5, just inside the viewing opening 14, a shield 42 is mounted for selective movement between positions wherein it blocks one or the other eye of the observer to facilitate the testing of one eye at a time. In addition, just beyond the shield 42 there is mounted a generally W-shaped frame 44 designed to receive selected optical lenses 45 for the purpose of varying the effective distance between the eye position 13 and the target 15, in accordance with conventional ophthalmic practice. In this way, an individual can be tested for visual acuity at different effective distances from the target 15. The lens holder 44 is supported by a shaft 46 having a control knob 47 on the outside of the housing by which the lens holder 44 can be rotated between a standing position in the observer's line of sight and a lowered, inoperative position.

A separate control console 50 includes manually actuated elements for controlling all of the functions of this testing apparatus. More specifically, knobs 51, 52 and 53 operate rotary potentiometers inside the console which control the intensity, respectively, of the projector bulb 35, the beam projectors 40', and the projectors 16 which illuminate the target 15. Similarly, switch buttons 55, 56 and 57 operate switches controlling the lamp 35 and projectors 40 and 16. Each of these switches is a rocker switch having three positions, namely On, Off and a calibrating position to which it is set while the associated potentiometer is being adjusted to change the intensity of the related light source. During such calibration of a light source, the intensity thereof is displayed on the LED display lens 60 in any convenient units, e.g. an arbitrary scale of 1 to 100.

Special provision is made for simultaneously illuminating all of the peripherally arranged beam projectors 40 or any selected one thereof to provide a single radially positioned glare source. A knob 61 controls a rotary selector switch having three positions, namely an Off position, a position in which it causes all of the projectors 40 to be energized, and a position wherein it causes only one of the projectors 40 to be energized. Another knob 62 controls a 12-position rotary selector switch which is used in conjunction with the third position of the switch knob 61 to select which one of the beam projectors 40 is to be energized.

The console 50 also houses a timer having a digital read-out on the display lens 60 for use during certain test operations such as the measurement of photo-stress and glare recovery times. A push button switch 65 controls the starting and stopping of this timer. The other pair of push buttons 66-67 may be used to actuate switches which control the motor drive for the slide mechanism as already described.

FIGS. 6-8 illustrate different glare conditions which can be produced during the use of this apparatus for glare testing. Thus in FIG. 6, a single one of the projectors 40 is energized, and as already noted, any single one of these projectors can be selected for energizing by means of the selector switch knob 62. FIG. 7 illustrates another condition wherein only the central glare beam is produced, by energizing of the lamp bulb 25. FIG. 8 shows the maximum number of glare sources energized, namely the central beam lamp 25 and all of the peripheral projectors 40. As also already noted, the intensity of the lamp 25 and the projectors 40 can be regulated independently of each other, as is also true of the projectors 16 which illuminate the target 15.

In using the apparatus of the invention to test the glare sensitivity of an individual, successive targets 15 are positioned for viewing under conditions of glare which are varied in intensity and location as described, with the observer reporting the location of the patch of the lowest contrast which she or he can identify. The results obtained with different charts and different glare conditions are compared with those obtained in the absence of glare to determine the individual's glare sensitivity. In addition, the apparatus of the invention can be used with only successive targets being illuminated to determine the basic contrast and spatial frequency sensitivity of an individual, under varying conditions of luminance of the target by varying the intensity of the light beam projectors 16 which illuminate the target.

Among the eye properties which can be tested with the apparatus of the invention is night vision, by suitable regulation of the luminance of the target 15 with all of the glare sources cut off. Also, the provision of means for inserting lenses before the eyes of the observer make it possible to test both near and far contrast sensitivity under varied testing conditions including the presence and absence of glare. Further, the provision of a timer facilitates the testing of glare recovery by measuring the improvement in contrast sensitivity beginning immediately after the glare sources are cut off. Thus the apparatus of the invention makes it possible to test near and far contrast sensitivity, as well as visual acuity, three types of glare sensitivity, photo-stress, night vision and glare recovery, with all the components needed for such testing being contained within a housing of convenient size and proportions, and with all such testing controlled from a single convenient manual control console.

While the methods herein described, and the forms of apparatus for carrying these methods into effect, constitute preferred embodiments of this invention, it is to be understood that the invention is not limited to these precise methods and forms of apparatus, and that changes may be made in either without departing from the scope of the invention, which is defined in the appended claims.

What is claimed is:

1. Apparatus for measuring the visual contrast sensitivity of an individual in both the presence and absence of glare, comprising:
   (a) a target having thereon alternating light and dark areas arranged for testing the visual contrast sensitivity of an individual,
   (b) means for locating one eye of an individual to be tested at a predetermined viewing position relative to said target,
   (c) means establishing a plurality of discrete glare source locations within the field of view of said target from said viewing position from which glare may be projected toward said viewing position, and
   (d) selective means for producing glare at any one or more of said source locations.

2. Apparatus as defined in claim 1 wherein said glare producing means comprises an array of discrete light beam sources arranged in said field of view in surrounding elation with the line of sight between said eye position and said target.

3. Apparatus as defined in claim 2 further comprising selectively operable means for creating veiling glare by collective energizing of all of said beam sources.

4. Apparatus as defined in claim 2 further comprising an additional light beam source arranged to project a light beam through the center of said target and said field of view, first selection means for selectively energizing any one of said array of light sources, second selection means for creating veiling glare by collective energization of all of said light sources, and selectively operable means for energizing said additional light beam source.

5. Apparatus as defined in claim 4 wherein said target is substantially opaque, and further comprising means for illuminating said target from the side thereof facing said eye position, and means for regulating the intensity of said illuminating means.

6. Apparatus as defined in claim 1 wherein said glare producing means comprises a light beam source located to project a light beam through the center of said target and said field of view.

7. Apparatus as defined in claim 1 further comprising selectively operable means for regulating the intensity of said glare producing means.

8. Apparatus as defined in claim 1 further comprising lens means selectively positionable in the line of sight between said target and said eye position for varying the apparent distance therebetween.

9. Apparatus as defined in claim 1 wherein said target is substantially opaque, and further comprising means for illuminating said target from the side thereof facing said eye position, and means for regulating the intensity of said illuminating means.

10. The method of measuring the visual acuity of an individual in both the presence and absence of glare which comprises the steps of:
    (a) locating one eye of an individual to be tested at a predetermined viewing position relative to a target having thereon multiple individual areas which differ from each other in contrast,
    (b) establishing a plurality of discrete glare source locations within the field of view of said target from said viewing position from which glare may be projected toward said viewing position,
    (c) while said target is being observed by said eye, producing glare at any one or more of said discrete source locations, and
    (d) determining the relationship of the resulting glare condition to the ability of such eye to detect the difference between said target areas.

11. The method defined in claim 10 comprising the further step of regulating the intensity of said glare condition in conjunction with said determining step.

12. The method defined in claim 11 further comprising the step of calibrating the intensity of said glare condition in predetermined increments.

13. The method defined in claim 10 wherein said determining step comprises the component steps of discontinuing said glare condition, and measuring the time required for such eye to recover from the exposure to said glare condition.

14. The method defined in claim 10 comprising the further step of varying the intensity of said glare condition concurrently with said determining step.

15. The method defined in claim 10 wherein said target is opaque and is illuminated from the side facing the observer, and further comprising the step of varying the luminance of said target in conjunction with said determining step.

16. The method defined in claim 10 wherein glare is produced in substantially surrounding relation with the position of said target in said field to view.

17. The method defined in claim 10 wherein glare is produced at a single position within said field of view in radially spaced relation with the center thereof.

18. The method defined in claim 10 wherein glare is produced in centered relation with said target.

* * * * *

UNITED STATES PATENT AND TRADEMARK OFFICE
CERTIFICATE OF CORRECTION

PATENT NO. : 4,800,404

DATED : January 24, 1989

INVENTOR(S) : Arthur P. Ginsburg et al

It is certified that error appears in the above-identified patent and that said Letters Patent is hereby corrected as shown below:

Column 5, line 38, "elation" should be --relation--.

Column 6, line 26, "said" should be --such--.

Signed and Sealed this

Thirty-first Day of October, 1989

Attest:

DONALD J. QUIGG

Attesting Officer

Commissioner of Patents and Trademarks